United States Patent
Lautenschläger et al.

(10) Patent No.: US 9,001,965 B2
(45) Date of Patent: Apr. 7, 2015

(54) METHOD FOR REPRESENTING THE RADIATION EXPOSURE OF AN EXAMINATION AREA OF AN OBJECT CAUSED BY RADIOLOGICAL IMAGING AND CORRESPONDING IMAGING DEVICE

(75) Inventors: Stefan Lautenschläger, Hausen (DE); Michael Pflaum, Röttenbach (DE)

(73) Assignee: Siemens Aktiengesellschaft, München (DE)

(*) Notice: Subject to any disclaimer, the term of this patent is extended or adjusted under 35 U.S.C. 154(b) by 377 days.

(21) Appl. No.: 13/528,887

(22) Filed: Jun. 21, 2012

(65) Prior Publication Data
US 2013/0003915 A1    Jan. 3, 2013

(30) Foreign Application Priority Data
Jul. 1, 2011    (DE) .......................... 10 2011 078 529

(51) Int. Cl.
| | |
|---|---|
| *G01N 23/083* | (2006.01) |
| *H05G 1/56* | (2006.01) |
| *A61B 6/03* | (2006.01) |
| *A61B 6/00* | (2006.01) |

(52) U.S. Cl.
CPC .............. *A61B 6/032* (2013.01); *A61B 6/5217* (2013.01); *A61B 6/542* (2013.01); *A61B 6/4441* (2013.01); *A61B 6/5235* (2013.01); *A61B 6/547* (2013.01)

(58) Field of Classification Search
CPC ....... A61N 5/00; A61N 5/103; A61N 5/1048; A61N 5/1064; A61N 5/1071; A61N 5/1075; A61B 6/00; A61B 6/025; A61B 6/42; A61B 6/50; A61B 6/52; A61B 6/5217; A61B 6/54; A61B 6/542; A61B 6/58; A61B 5/00; A61B 5/01; A61B 5/015
USPC .............. 378/4–20, 62, 65, 91, 95, 98, 98.2, 378/98.5, 98.8, 98.12, 162, 165, 204, 207, 378/210, 901; 250/370.01, 370.07, 370.08, 250/370.09, 370.15, 491.1, 526; 382/128, 382/131, 162, 165, 325
See application file for complete search history.

(56) References Cited

U.S. PATENT DOCUMENTS

| | | | |
|---|---|---|---|
| 6,920,202 B1* | 7/2005 | Dinsmore ...................... | 378/119 |
| 2007/0201617 A1* | 8/2007 | Nakayama et al. ............ | 378/108 |
| 2008/0247506 A1* | 10/2008 | Maschke ......................... | 378/15 |
| 2009/0175418 A1* | 7/2009 | Sakurai et al. ................ | 378/98.5 |
| 2010/0094119 A1* | 4/2010 | Yu et al. ......................... | 600/411 |
| 2010/0290591 A1* | 11/2010 | Spahn ........................... | 378/98.5 |
| 2012/0128125 A1* | 5/2012 | Jabri et al. ...................... | 378/62 |

FOREIGN PATENT DOCUMENTS

EP    0212793 B1    1/1991

* cited by examiner

*Primary Examiner* — Anastasia Midkiff (57) ABSTRACT

A method for representing an exposure to radiation of an examination area of an object caused by radiological imaging is proposed. A 3D image of the examination area of the object being examined is acquired. Absorption coefficients of the examination area are determined. The radiation exposure of the examination area caused by radiological imaging is determined and is represented in the 3D image. A termination criterion is queried. The radiation exposure of the examination area is iteratively determined till the termination criterion is fulfilled.

11 Claims, 5 Drawing Sheets

METHOD FOR REPRESENTING THE RADIATION EXPOSURE OF AN EXAMINATION AREA OF AN OBJECT CAUSED BY RADIOLOGICAL IMAGING AND CORRESPONDING IMAGING DEVICE

CROSS REFERENCE TO RELATED APPLICATIONS

This application claims priority of German application No. 10 2011 078 529.9 filed Jul. 1, 2011, which is incorporated by reference herein in its entirety.

FIELD OF INVENTION

The present application relates to a method for representing the radiation exposure of an examination area of an object being examined which is caused or may be caused by a radiological imaging device. Furthermore, the present application relates to a radiological imaging device for carrying out a corresponding method.

BACKGROUND OF INVENTION

Medical diagnostic and intervention systems in neurology, angiography and cardiology nowadays use many X-ray devices or pieces of X-ray equipment as a basis for imaging. X-ray devices are frequently equipped with what is referred to as a C-arm. A C-arm usually comprises an X-ray source, also known as an X-ray emitter, and an X-ray detector positioned opposite by a connecting support embodied in the shape of a letter C. The C-arm can be mounted to a stand or to the ceiling and can be moved to different positions by jointed connections. In X-rays an object being examined, e.g. a patient, is irradiated with X-ray beams. If X-ray beams penetrate a body, they are attenuated or absorbed to varying degrees depending on the material involved, such as bones, different types of tissue or fluid, so that when the X-ray detector is struck, different intensity patterns or images are produced corresponding to the materials penetrated.

When material is penetrated, radiation supplies energy to the surrounding atoms or molecules. Electrons from the atomic shells can also be struck and chemical bonds can be broken. Radicals are produced, which for their part can again cause damage. Difficult examinations or interventions, such as for example clamping an aneurysm in a neurosurgical operation, often require frequent irradiation of the affected body region over an extended period of time. This means that the patient is subjected to significant radiation exposure or radiation levels. Added to this is the difficulty that a physician performing the treatment is reluctant to alter the position of the X-ray device which is favorable in terms of imaging, which means that the same region of the body is constantly irradiated over a long period of time. This can lead to radiation damage in the volume of the body region being irradiated and to a heating of the irradiated area or surface which may even amount to skin burns. This is also referred to as a hotspot, which is created by the X-ray fan beam.

In practice, after a certain number of X-ray recordings, a physician will alter the recording direction, which is also described as the projection setting of the X-ray device, e.g. by rotation of the C-arm, in order to distribute the radiation levels over a larger volume or a larger surface area. This, however, presupposes a considerable amount of experience and discipline on the part of the physician.

Modern X-ray devices offer the possibility, under the abbreviation CARE, which stands for Combined Applications to Reduce Exposures, to add together the radiation doses of several X-ray recordings and to issue a warning if a limit is exceeded. The disadvantage of these systems is that even if the changes to the projection setting are only slight, e.g. when turning the C-arm by one or two degrees, the sum of the radiation applied is reset to zero, even though a point may continue to be radiated when the position of the C-arm has been slightly altered.

SUMMARY OF INVENTION

The object of the present application is therefore to specify a method for representing the radiation exposure of an examination area of an object being examined in radiological imaging. Furthermore the object consists in specifying a radiological imaging device which enables a representation of the radiation exposure of an examination area of an object being examined in radiological imaging.

The application achieves this object by a method for representing the radiation exposure of an examination area of an object being examined caused by a radiological imaging device having the features of the first independent claim and a radiological imaging device having the features of the second independent claim.

The fundamental idea behind the application is a method for representing the radiation exposure of an examination area of an object being examined caused by a radiological imaging device, which method comprises the following method steps:
S1) Acquisition of a 3D image of the examination area of the object being examined;
S2) Determination of absorption coefficients of the examination area;
S3) Determination of the radiation exposure of the examination area which is caused or may be caused by radiological imaging;
S4) Representation of the radiation exposure of the examination area in the 3D image of the examination area of the object being examined;
S5) Querying of a termination criterion and if the termination criterion is not fulfilled, a jump to method step S3.

The first inventive method step relates to the acquisition of a 3D image of an examination area of an object being examined. The object being examined can be, for example, a human patient who is to be examined or on whom a medical intervention is to be performed. An examination area is understood to be a spatial subset of the object under examination, which is to be examined by a radiological imaging device or within which a medical intervention is to take place. For example, the examination area in a neurological intervention can comprise the patient's head. In a stent angioplasty the examination area comprises the volume, which encloses the vessel in which a stent is to be inserted. The 3D image of the spatial examination area can be obtained by an imaging method from the prior art, such as computed tomography, CT, or magnetic resonance tomography, MR. Modern angiography systems are able to record three-dimensional images of the examination area by rotation of the C-arm around the patient and reconstruction of the rotation sequences so that these systems can be used advantageously both for obtaining the 3D image of the examination area and for ensuing radiological examination or radiological intervention.

In the second inventive method step, the absorption coefficients of the spatial examination area are determined. These result directly from the 3D image or can be calculated from the 3D image information. Absorption coefficients, density values, linear attenuation coefficients, gray values and HU values, i.e. absorption values in Hounsfield units, can be calculated with the aid of formulae known from the prior art, so that the absorption coefficients can also be obtained from values which are present in one of the units mentioned. The result of the determination of absorption coefficients is a three-dimensional matrix, the elements of which represent the absorption coefficients of the volume elements of the spatial examination area. The size of the absorption coefficient matrix can, for example, be equal to the size of the 3D image of the examination area. A single volume element is also described as a voxel.

The third method step of the inventive method comprises the determination of the radiation exposure of the spatial examination area which is caused or may be caused by radiological imaging. This means that the radiation exposure, which may be caused by an X-ray device or a piece of X-ray equipment, is determined for the spatial examination area, i.e. for each voxel of the spatial examination area. For this it may be necessary to register the volume in the spatial examination area, such as in the 3D image of the examination area, which can be penetrated by radiological imaging.

In the fourth method step, the radiation exposure of the examination area is displayed in the 3D image of the examination area of the object being examined. In this case the degree of radiation exposure can be represented for example in the form of a color code, a known color schemes, such as transparent for no radiation exposure, green for slight radiation exposure and yellow to red for significant radiation exposure. The allocation of radiation exposure value and color can be prescribed by a user, wherein for example a clinic-specific or country-specific limit or a limit from radiation protection guidelines is assigned to the color that represents the maximum radiation exposure or risk, e.g. the color red. The last inventive method step comprises the querying of a termination criterion and if the termination criterion is not fulfilled comprises a jump to the third method step. The termination criterion can, for example, be understood to be the switching state of a switch, such as an on/off switch, the activation of a button or the end of a duration which can be chosen.

One embodiment of the application proposes that at least one selectable parameter of the radiological imaging device, such as a selectable projection geometry and/or a selectable radiation dose and/or a voltage which may be supplied to an X-ray source of the radiological imaging device, is used in the determination of the radiation exposure of the area being examined which may be caused by radiological imaging. Parameters of the projection geometry are for example the spatial position of detector and X-ray source in relation to the examination area. The spatial position is determined, on the other hand, by the orientation or alignment of the C-arm of the X-ray device and the distance from the detector and X-ray source to the examination area. The radiation dose is, for example, influenced by the duration of the X-ray irradiation. The electrical voltage has a significant influence on the absorbed radiation, usually specified in kilovolts (kV), with which the X-ray source, such as an X-ray tube, is operated. Usual values are 25 kV to 35 kV for the representation of tissue, for example in a mammography, and up to 120 kV for a representation of bones, for example. With lower voltage values, a larger proportion of the radiation is absorbed by the tissue. Further influence variables on radiation exposure can be parameters of focusing devices or ray filters, e.g. collimators. The radiological imaging parameters selected at the time of determining the radiation exposure are used in determining the radiation exposure. A further possibility would be to select one or more parameters of the radiological imaging merely for determining the radiation exposure and supply these to a calculation algorithm for the radiation exposure without applying the parameters to the imaging device. Since in this embodiment of the application no actual radiological imaging takes place, the radiation exposure of the examination area is to be regarded as simulated radiation exposure which would arise if radiological imaging were to be carried out with the selected parameters. This method helps a physician in so far as he can judge even prior to taking an X-ray the possible consequences in terms of radiation exposure of the examination area.

A further advantageous embodiment of the application proposes that the determination of the radiation exposure of the examination area takes place after radiological imaging, wherein at least one parameter of the radiological imaging device selected during imaging, such as a projection geometry and/or a radiation dose and/or a voltage supplied to an X-ray source of the radiological imaging device, is used in the determination of the radiation exposure of the examination area.

In this embodiment of the application, to determine the radiation exposure of the spatial examination area, specifically those parameters of the radiological imaging device which were set at the time of the recording are used.

In a further advantageous embodiment of the application, the determination of the radiation exposure of the examination area comprises accumulation of the radiation exposure. If several X-ray recordings are made of an examination area, e.g. during a digital subtraction angiography (DSA) or during a fluoroscopy, the examination area is exposed to X-ray radiation with each X-ray recording. This situation is taken into account by summation of the individual radiation exposures. The radiation exposure value of the examination area is expediently set to zero at the beginning of a radiological examination or intervention. Each radiological imaging then adds the radiation exposure associated with each voxel.

In an advantageous development of the application the representation of the radiation exposure of the examination area comprises a maximum function and/or an, such as color-coded, 2D projection. The disadvantage of a spatial representation of the radiation exposure, which is possible by determining the radiation exposure for each voxel of the 3D image, is that it is difficult to interpret due to the large amount of information or that important areas, e.g. those with greater radiation levels, are concealed by less important areas, e.g. areas with lower radiation levels. A function, which only represents the maximum radiation level values in a 2D projection, advantageously restricts the information to what is essential, e.g. the representation of areas with high radiation levels. In other words, the radiation exposure is determined for each voxel and the maximum values of all voxels, which are arranged on a ray perpendicular to a projection direction or direction of view, are displayed in a 2D projection. Furthermore, the representation can be interpreted as a color-coded maximum intensity projection, or MIP, of the volume.

A further advantageous embodiment of the application proposes that after the radiation exposure of the examination area is determined, the temperature is determined from the examination area, wherein values from the determined radiation exposure are used in the determination of the temperature, and that the temperature is represented in the 3D image of the examination area of the object being examined. In addition to the determination of the radiation exposure of the examination area, i.e. determining the quantity of radiation absorbed for each voxel of the examination area according to one of the previously described methods, the determination and representation of the temperature for each voxel, or the heating of the irradiated region or the irradiated surface, can be of significant interest to a physician in radiological imaging, since the absorption of ionizing radiation is associated with a heating of the absorbing tissue and can also lead to damage. The link between radiation exposure and temperature or heating of the examination area can, for example, be determined by a series of tests or be taken from scientific literature, for example in the form of a radiation exposure-temperature model. Qualitatively, e.g. high-intensity X-ray radiation leads to a relatively small increase in temperature due to increased penetration compared to weaker radiation as is typically used during a fluoroscopy. If the temperatures of several voxels, e.g. along a straight line, are added together, a temperature distribution can be determined, which gives a physician further information about temperature areas which may be critical.

Advantageously the determination of the temperature from the examination area includes a decrease in temperature as a function of time. The human body has the ability to regulate its temperature within certain limits and to reduce an increased temperature, such as that caused by exposure with X-ray radiation. If the temperature from the examination area is based on a model of the decline over time of a temperature increase which can be determined e.g. from a series of tests or can be taken from scientific literature, the temperature can be determined more realistically. For example an examination area, which has achieved a critical temperature at a first point in time, can be cooled again by waiting, e.g. ten minutes so that the recording of a further X-ray image is uncritical in relation to temperature.

An embodiment of the application proposes that the representation of the temperature from the examination area comprises a maximum function and/or a 2D projection, which is a color-coded. Similar to the embodiments for representing the radiation levels, a function which only represents the maximum temperature values in a 2D projection, advantageously restricts the information to what is essential, e.g. the representation of areas with a high temperature. The temperature of each voxel is thus determined and the maximum values of all voxels which lie on a ray perpendicular to a direction of projection or direction of view are displayed in a 2D projection.

An optical and/or acoustic warning signal is issued if at least one value of the determined radiation exposure from the examination area or the temperature of the examination area exceeds a prescribed limit. Through this embodiment a person who is using the radiological imaging device is warned as soon as at least one value of the determined radiation exposure of the examination area or a temperature value from the examination area exceeds a limit value for the radiation level or temperature. Here, it can for example also be a clinic- or country-specific limit or a limit from radiation protection guidelines. An optical warning signal can be understood to be, for example, a flashing colored surface of the area which exceeds the limit value or the insertion of a warning logo or warning text. An acoustic warning signal can for example be a warning sound.

A further fundamental idea behind the application relates to a radiological imaging device comprising a C-arm, an X-ray source, an X-ray detector and a control and display device, wherein the control and display device is embodied to process an acquired 3D image of an examination area of an object being examined, determine absorption coefficients of the examination area, determine radiation exposure of the examination area which is caused or may be caused by radiological imaging, represent the radiation exposure of the examination area in the 3D image of the examination area of the object being examined and query a termination criterion.

The control and display device of the radiological imaging device is advantageously embodied to carry out one of the previously described methods.

BRIEF DESCRIPTION OF THE DRAWINGS

The exemplary embodiments described in more detail in the following represent embodiments of the present application. Further advantageous developments emerge from the following figures together with the description.

DETAILED DESCRIPTION OF INVENTION

Figure 1:
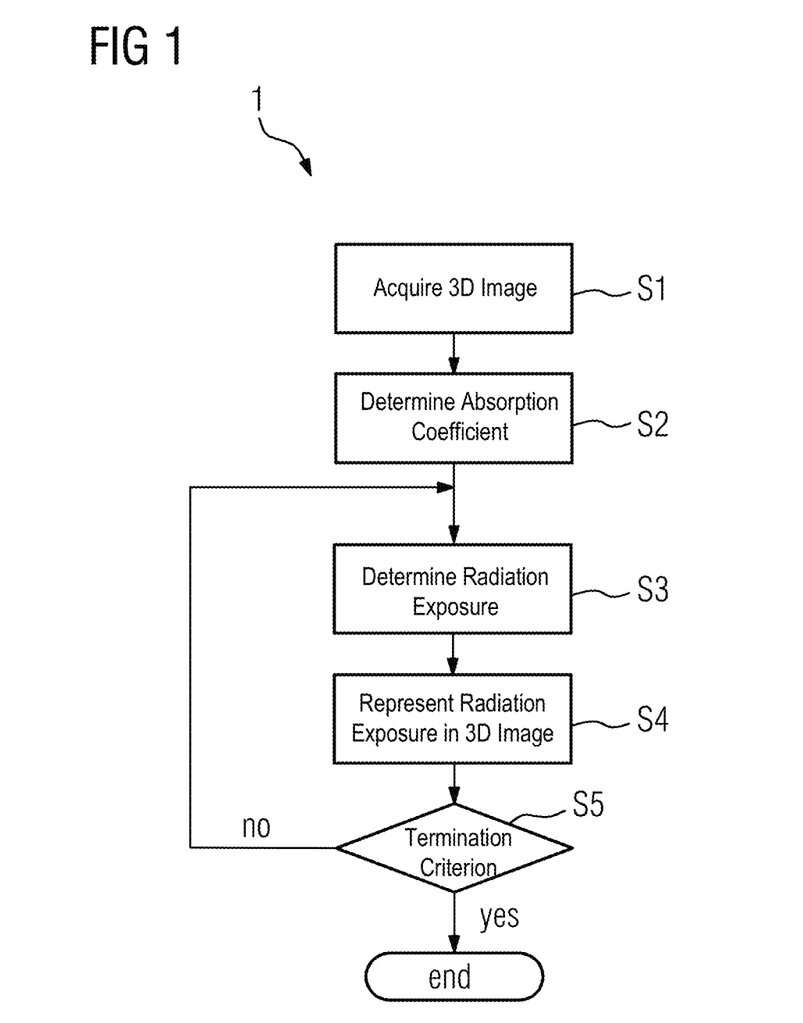
FIG. 1 shows a flow diagram of an inventive method for representing the radiation exposure of an examination area of an object being examined.

FIG. 1 shows a flow diagram of an inventive method 1 for representing radiation exposure of an examination area 30 of an object being examined 31. The method 1 comprises the method steps S1 to S5:

S1) Acquisition of a 3D image 49 of the examination area 30 of the object being examined 31;

S2) Determination of absorption coefficients of the examination area 30;

S3) Determination of the radiation exposure of the examination area 30 which is caused or can be caused by radiological imaging;

S4) Representation of the radiation exposure of the examination area 30 in the 3D image 49 of the examination area 30 of the object being examined 31;

S5) Querying of a termination criterion and if the termination criterion is not fulfilled, a jump to method step S3.

Figure 2:
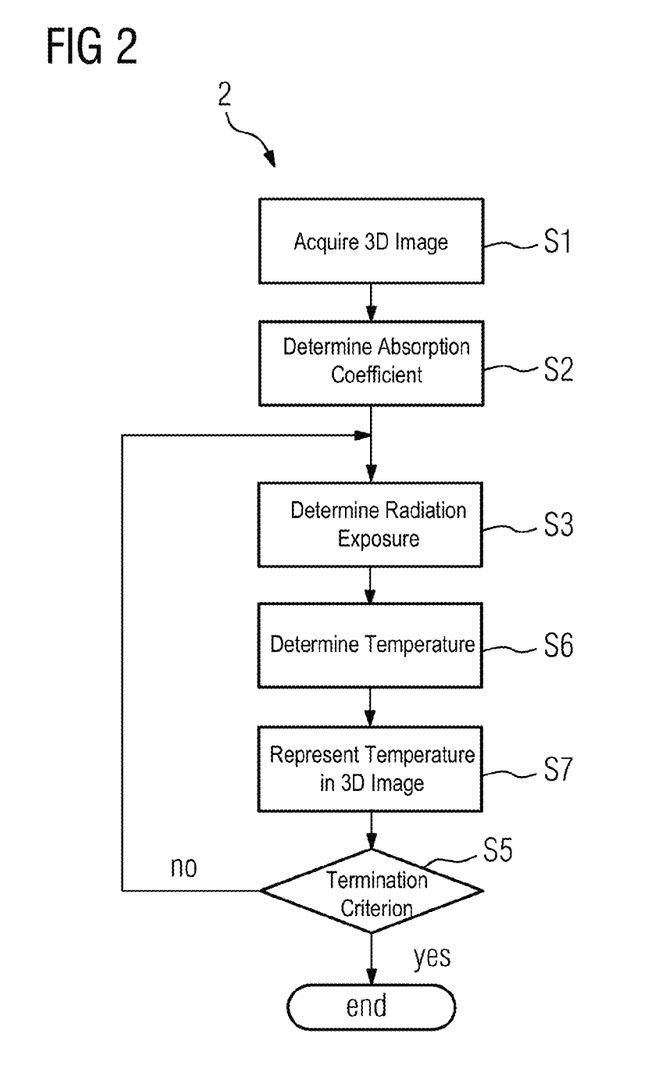
FIG. 2 shows a further flow diagram of an inventive method for representing the temperature from an examination area which is caused by radiation exposure of an examination area of an object being examined.

FIG. 2 shows a flow diagram of a further inventive method 2 for representing a temperature from an examination area which is caused by the radiation exposure of an examination area 30 of an object being examined 31. The method 2 comprises the method steps S1 to S3 and S5 to S7:

S1) Acquisition of a 3D image 49 of the examination area 30 of the object being examined 31;

S2) Determination of absorption coefficients of the examination area 30;

S3) Determination of the radiation exposure of the examination area 30 which is caused or may be caused by radiological imaging.

S6) Determination of a temperature from the examination area 30, wherein values from the determined radiation exposure are used in the determination of the temperature;

S7) Representation of the temperature from the examination area 30 in the 3D image 49 of the examination area 30 of the object being examined 31;

S5) Querying of a termination criterion and if the termination criterion is not fulfilled, a jump to method step S3.

Figure 3:
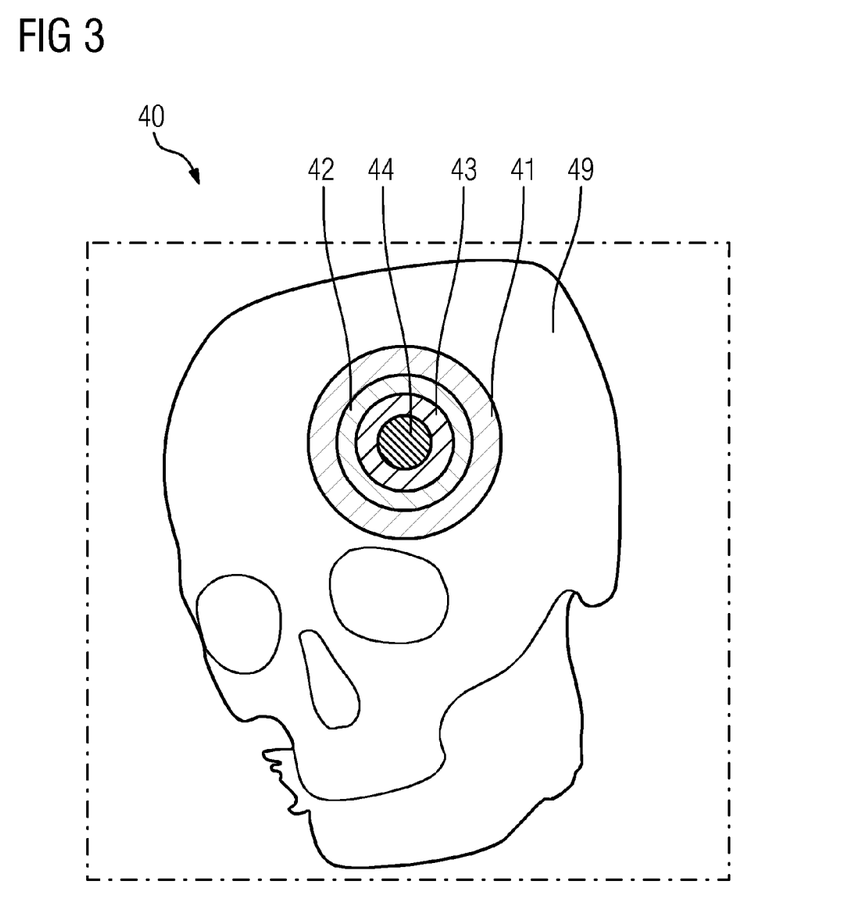
FIG. 3 shows an exemplary embodiment of the representation of the radiation exposure of an examination area.

FIG. 3 shows an exemplary embodiment of a representation 40 of the radiation exposure of an examination area 30. The examination area 30 is the head of a patient 31. By an imaging method from the prior art, such as computed tomography, magnetic resonance tomography or a modern angiography system, a spatial image, a 3D image 49, of the spatial examination area 30 was obtained. This 3D image is present, e.g. in the form of a three-dimensional matrix, wherein the elements of the matrix correspond to the gray values of the image. For further imaging, for example in the context of a medical intervention, a C-arm X-ray device is used. In a second method step the absorption coefficients of the spatial examination area 30 are determined. These can be derived from the gray values of the 3D image 49. Absorption coefficients, density values, linear attenuation coefficients, gray values and HU values can be converted to one another, so that the absorption coefficients can even be obtained from values which are present in one of the units mentioned. As a result a three-dimensional matrix, is obtained, for example, the elements of which represent the absorption coefficients of the volume elements of the spatial examination area 30. The size of the absorption coefficient matrix is equal to the size of the 3D image 49 of the examination area 30. A single volume element is also described as a voxel. In the third method step, the radiation exposure of the spatial examination area 30 is determined by radiological imaging. This means that the radiation exposure, which can be caused by recordings made by the X-ray device, is determined for the spatial examination area 30, i.e. such as for each voxel of the spatial examination area 30. It can be necessary here, e.g. when the 3D image 49 is obtained with an imaging device other than the X-ray device, to register the volume in the spatial examination area, i.e. in the 3D image of the examination area 30, that can be penetrated by radiological imaging. Registration or image registration is understood in digital image processing to mean bringing two or more images of the same image motif or at least similar motifs in line with each other as far as possible. Parameters of the X-ray device, such as projection geometry, radiation dose or voltage, with which the X-ray source of the X-ray device is controlled, are used in the determination of the radiation exposure. The radiation exposure can even be determined before an X-ray recording is carried out. This means that the currently selected parameters of the X-ray device or parameters that can be predetermined which are, however, not supplied to the X-ray device are regarded as input variables. Thus it is a simulated radiation exposure which helps a physician to assess the consequences of an X-ray recording even prior to the actual recording. In the fourth method step the radiation exposure of the examination area 30 is represented in the 3D image 49 of the examination area 30 of the object being examined 31. The representation of the degree of radiation exposure can take place here, for example, in the form of a color code, wherein known color schemes are used such as transparent for no radiation exposure, green for slight radiation exposure and yellow to red for significant radiation exposure. The allocation of radiation exposure value and color can be prescribed by a user, wherein for example a clinic- or country-specific limit or a limit from radiation protection guidelines is assigned a color that represents the maximum radiation exposure or risk, e.g. the color red.

In FIG. 3 four areas 41 to 44 are represented, by way of example, which illustrate the radiation exposure of the examination area 30. The originally determined spatial radiation exposure, i.e. the radiation exposure of each voxel of the examination area, is subject to a maximum function and is then displayed in the 3D image 49 as a 2D projection. The area 41 represents lower radiation levels than the area 44, which, for example, has the highest radiation levels. Areas 42 and 43 lie in-between. Advantageously when at least one parameter of the X-ray device is changed, e.g. the orientation of the C-arm or the distance from the X-ray source to the examination area 30, the determination of possible radiation exposure is carried out again and displayed. The 3D image 49 is synchronized with the projection geometries of the X-ray device, i.e. the 3D image 49 is rotated for example when the alignment of the C-arm is changed in a corresponding manner. The method is carried out until a termination criterion, for example the activation of a switch, is fulfilled.

Figure 4:
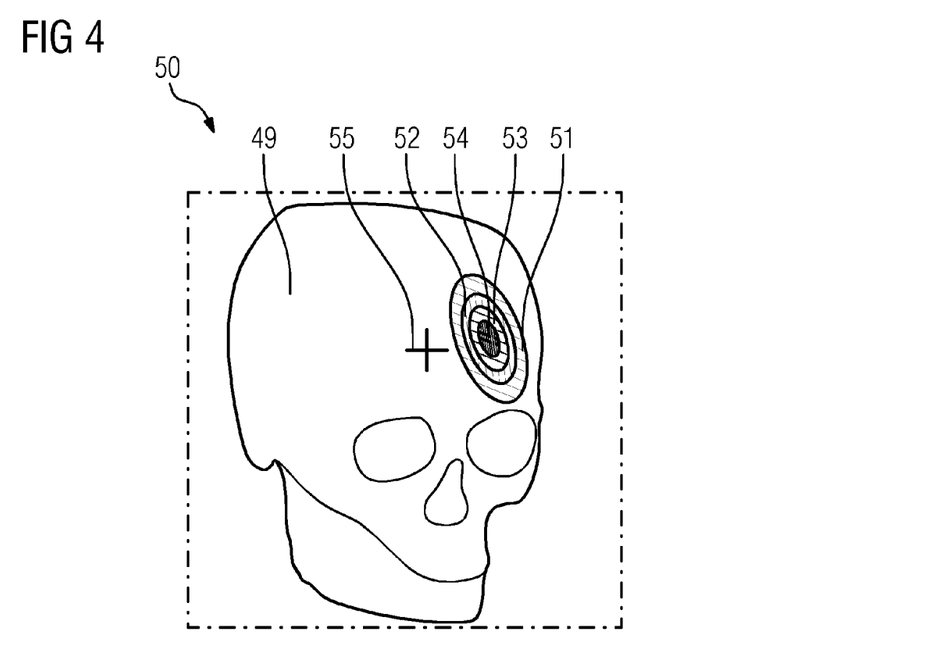
FIG. 4 shows an exemplary embodiment of a representation of the radiation exposure of an examination area after radiological imaging.

In FIG. 4, an exemplary embodiment of a representation 50 of the radiation exposure of an examination area 30 is reproduced after radiological imaging. The acquisition of a 3D image 49 of the examination area 30 of an object being examined 31 and the determination of absorption coefficients of the examination area 30 can take place in the same way as described in the description of FIG. 3. The determination of the radiation exposure of the examination area 30 caused by radiological imaging takes place here after an X-ray image has been recorded. The parameters of the X-ray device which are set during the recording, such as projection geometry, radiation dose, exposure time, voltage applied to the X-ray source of the X-ray device, settings of focusing devices or ray filters, e.g. collimators, are used in the determination of the radiation exposure. The radiation exposure is determined for each voxel of the examination area 30. The maximum values of all voxels are for example displayed in a 2D projection on the 3D image 49 and these lie on a ray perpendicular to the direction of view onto the 3D image 49. The result of the determined radiation exposure is displayed in the 3D image 49 of the examination area 30. It shows schematically four areas 51 to 54 of differing radiation levels. Area 54 has radiation levels which are larger than the radiation level limit which is set down e.g. in radiation protection regulations, and is therefore made known by an optical warning message, e.g. in the form of a particularly striking color. The radiation exposure values are stored in this exemplary embodiment and the representation of the radiation exposure is also retained when the C-arm of the X-ray device is moved and the 3D image is simultaneously adjusted. The cross 55 shows the central point of the current projection setting of the X-ray device. This makes it easier for a physician carrying out the treatment to find a favorable position of the X-ray device in relation to the imaging and to find a region of the examination area that has until now been subjected to only low levels of radiation.

Figure 5:
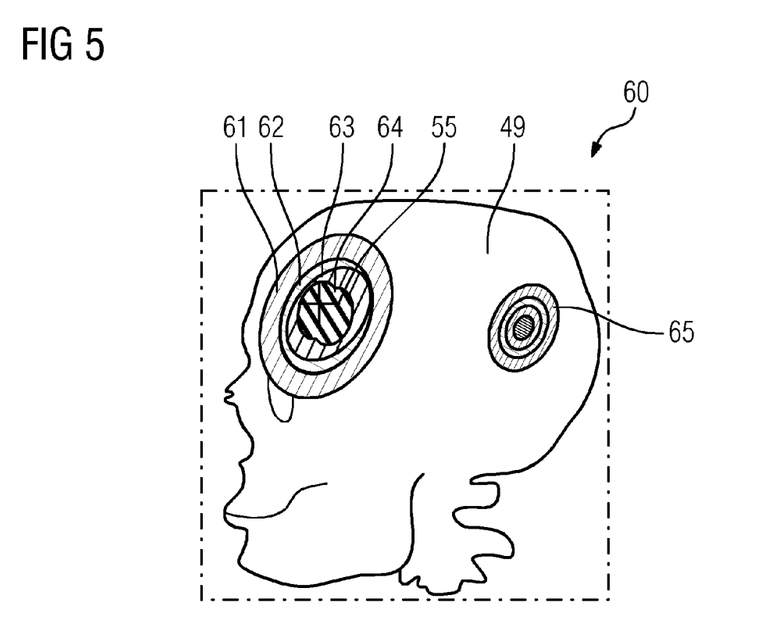
FIG. 5 shows a representation of the radiation exposure and a temperature of an examination area of an object being examined during a radiological examination.

FIG. 5 shows an exemplary embodiment of a representation 60 of the radiation exposure 65 and a temperature 61 to 64 from an examination area 30 of an object being examined 31 during a radiological examination. The radiation exposure 65 can be represented according to a method as per the description of FIG. 3. After the determination of the absorbed quantity of radiation for each voxel of the examination area, the heating of the area examined can be determined, since the absorption of ionizing radiation is associated with a heating of the absorbing tissue. The reference characters 61 to 64 show the schematic representation of temperature. The area 61 is heated less than the area 64. Areas 62 and 63 have a temperature between the temperatures of areas 61 and 64. In this exemplary embodiment, the change over time of the heating, caused by further X-ray recordings and of the cooling, caused by the natural ability of humans to counteract heating, e.g. by blood circulation or sweating, is taken into consideration when determining the temperature. Empirical or physical models are used for this purpose which for example determine the temperature of the material which is represented by the voxel as a function of time, the absorption coefficients and the parameters of the X-ray device. The radiation and temperature values are furthermore taken into consideration when the projection settings are altered. For example in FIG. 5 it is to be recognized from the kidney-shaped form of the surface 64 and the center 55 of the current projection setting of the X-ray device, that, for example, two X-ray images are recorded with slightly altered projection settings. A user of the method can select whether a determination and representation of the radiation exposure and temperature should take place as soon as an X-ray recording has been made or even prior to an X-ray recording, e.g. with the projection settings and X-ray parameters that are currently set. The latter case has the advantage that a physician can assess the consequences of an X-ray recording and may adapt the projection settings when there is a risk of the radiation exposure or temperature being too high.

Figure 6:
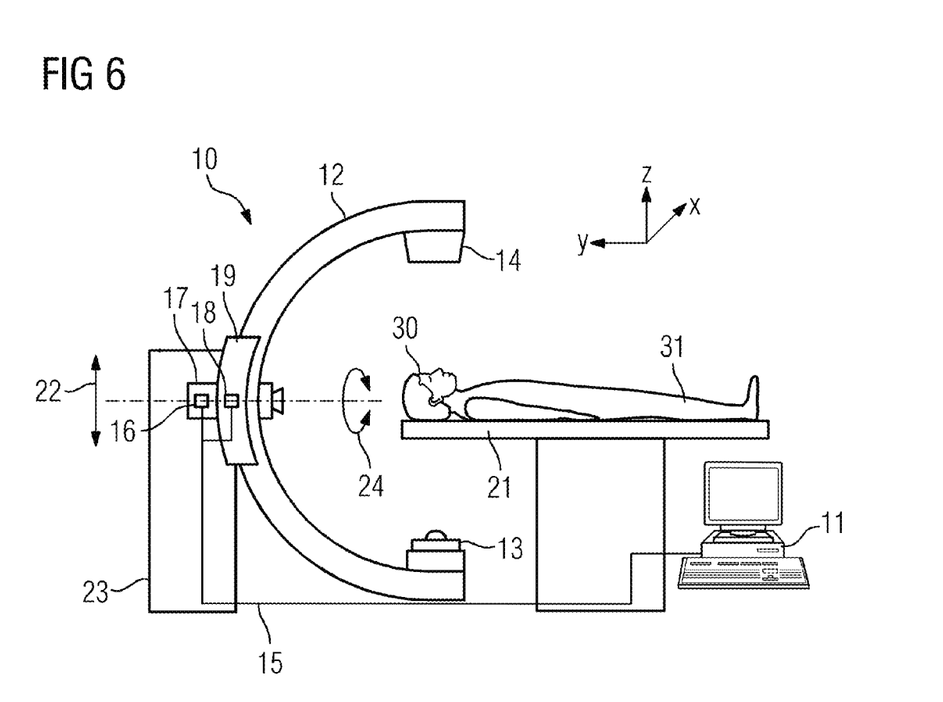
FIG. 6 shows a schematic representation of an inventive radiological imaging device.

FIG. 6 is a schematic representation of an embodiment of an inventive radiological imaging device 10, a so-called C-arm X-ray device. It comprises a C-arm 12, on which an X-ray source 13 and an X-ray detector 14 are mounted in opposing arrangement. The C-arm is connected in a jointed manner to a stand 23. An object being examined 31, in this case a patient, is positioned on a positioning device 21, in this case an examination table. The examination area 30 is the patient's head, which is to be recorded with the aid of an X-ray device. The C-arm 12 can be moved in the z-direction, i.e. in the vertical direction 22, by a first actuator 17, e.g. an electric motor. The C-arm 12 can be rotated about an axis which is parallel to the y axis, i.e. about a horizontal axis, by a second actuator 19, e.g. an electric motor with toothed gearing, which is shown by the reference number 24. By moving the C-arm 12, the position of the X-ray source 13 and the X-ray detector 14 changes relative to the examination area 30. A first sensor 16 and a second sensor 18 are mounted to the C-arm 12. A control and display device 11, for example an electronic computer, controls actuators 17 and 19 via a connection device 15, e.g. electrical cables, and receives signals from sensors 16 and 18, so that the projection settings are known to the control and display device 11. The control and display device 11 are embodied to transmit parameters of the X-ray device 10, such as radiation dose, the voltage supplied to the X-ray source 13 or exposure time, to the X-ray device to initiate recordings of X-ray images and receive X-ray images of the X-ray device 10. Furthermore the control and display device 11 is capable of receiving a 3D image of the examination area 30 which can also be obtained by another imaging device and carrying out digital imaging algorithms, such as medical ones, which are known from the prior art. An operating device, which for example is embodied as a switch or button, enables the querying of a termination criterion, for example to terminate calculations in the control and display device 11. According to the application, the control and display device 11 is embodied to process an acquired 3D image of the examination area 30 of the object being examined 31, determine absorption coefficients of the examination area 30, determine the radiation exposure of the examination area 30 which is caused or may be caused by radiological imaging, represent the radiation exposure of the examination area 30 in the 3D image of the examination area 30 and query a termination criterion.

The invention claimed is:

1. A method for representing a radiation exposure of an examination area of an object being examined caused by radiological imaging, comprising:

acquiring a 3D image of the examination area of the object by a radiological imaging device;
determining an absorption coefficient of the examination area by a control and display device;
determining the radiation exposure of the examination area by the control and display device;
representing the radiation exposure of the examination area in the 3D image displayed in the control and display device;
querying a termination criterion; and
repeating the step of determining the radiation exposure if the termination criterion is not fulfilled,
wherein the radiation exposure of the examination area is determined by a parameter of the radiological imaging device selected during the radiological imaging, and
wherein the method further comprises:
selecting the parameter of the radiological imaging device to be used during the radiological imaging prior to the acquisition of the 3D image;
simulating the radiation exposure of the examination area based on the selected parameter; and
assessing a consequence of the 3D image according to the simulated radiation exposure of the examination area.

2. The method as claimed in claim 1, wherein the parameter of the radiological imaging device comprises projection geometry, and/or radiation dose, and/or voltage supplied to an X-ray source of the radiological imaging device.

3. The method as claimed in claim 1, wherein the radiation exposure of the examination area is determined after the radiological imaging.

4. The method as claimed in claim 1, wherein the radiation exposure of the examination area is determined by an accumulation of the radiation exposure.

5. The method as claimed in claim 1, wherein the radiation exposure of the examination area is represented by a maximum function and/or a color-coded 2D projection.

6. The method as claimed in claim 1, wherein an optical and/or an acoustic warning signal is issued when the radiation exposure of the examination area exceeds a predetermined limit 7. The method as claimed in claim 1, wherein a temperature of the examination area is determined from the radiation exposure and is represented in the 3D image.

8. The method as claimed in claim 7, wherein the temperature of the examination area is determined by a decrease in the temperature as a function of time.

9. The method as claimed in claim 7, wherein the temperature of the examination area is represented by a maximum function and/or a color-coded 2D projection.

10. The method as claimed in claim 7, wherein an optical and/or an acoustic warning signal is issued when the temperature of the examination area exceeds a predetermined limit.

11. A radiological imaging device, comprising:
a C-arm having an X-ray source and an X-ray detector for acquiring a 3D image of an examination area of an object; and
a control and display device that is configured to:
acquire a 3D image of the examination area of the object by a radiological imaging device;
determine an absorption coefficient of the examination area by a control and display device;
determine the radiation exposure of the examination area by the control and display device;
represent the radiation exposure of the examination area in the 3D image displayed in the control and display device;

query a termination criterion; and
repeat the step of determining the radiation exposure if the termination criterion is not fulfilled,
wherein the radiation exposure of the examination area is determined by a parameter of the radiological imaging device selected during the radiological imaging, and
wherein the control and display device is further configured to:
select the parameter of the radiological imaging device to be used during the radiological imaging prior to the acquisition of the 3D image;
simulate the radiation exposure of the examination area based on the selected parameter; and
assess a consequence of the 3D image according to the simulated radiation exposure of the examination area.

* * * * *